United States Patent [19]

Nakamura et al.

[11] Patent Number: 6,096,312
[45] Date of Patent: Aug. 1, 2000

[54] AGENT FOR SUPPRESSING A REDUCTION OF CD4+ LYMPHOCYTES

[75] Inventors: Norio Nakamura; Kamon Shirakawa; Tomokazu Matsusue, all of Tokyo; Shigekazu Nagata, Suita, all of Japan; Man Sung Co, Cupertino; Maximiliano Vasquez, Palo Alto, both of Calif.

[73] Assignees: Mochida Pharmaceutical Co., Ltd., Tokyo; Osaka Bioscience Institute, Osaka-Fu, both of Japan

[21] Appl. No.: 08/999,631

[22] Filed: Jan. 22, 1998

Related U.S. Application Data

[63] Continuation-in-part of application No. 09/001,011, Dec. 30, 1997, abandoned, which is a continuation-in-part of application No. PCT/JP96/01820, Jul. 1, 1996, which is a continuation-in-part of application No. 08/649,100, May 17, 1996.

[30] Foreign Application Priority Data

Jun. 30, 1995 [JP] Japan .................................. 7-188480

[51] Int. Cl.[7] ...................... A61K 39/395; C07K 14/525; C07K 16/00
[52] U.S. Cl. ...................... 424/145.1; 424/148.1; 424/154.1; 424/172.1; 424/139.1; 435/332
[58] Field of Search ............... 424/145.1, 148.1, 424/154.1, 172.1, 139.1; 435/322; 530/388.2

[56] References Cited

U.S. PATENT DOCUMENTS

| | | | |
|---|---|---|---|
| 5,436,154 | 7/1995 | Barbeti et al. | 435/240 |
| 5,632,994 | 5/1997 | Reed et al. | 424/198.1 |
| 5,750,653 | 5/1998 | Chu et al. | 530/350 |

FOREIGN PATENT DOCUMENTS

| | | |
|---|---|---|
| 0675200 | 10/1995 | European Pat. Off. . |
| 2237935 | 9/1990 | Japan . |
| 8511692 | 12/1995 | Japan . |
| 9503672 | 4/1997 | Japan . |
| 9510540 | 4/1995 | WIPO . |
| 9513293 | 5/1995 | WIPO . |
| 9527735 | 10/1995 | WIPO . |
| 9629350 A1 | 9/1996 | WIPO . |
| 9712632 | 4/1997 | WIPO . |

OTHER PUBLICATIONS

Osband, Michael E. et al, Problems in the investigational study and clinical use of cancer immunotherapy, Immunology Today, vol. 11, No. 61990, pp. 193–195, 1990.

Okurma, Yasushi. Research Report for 1997 Project for Promoting the AIDS Pharmaceuticals Development with English Translation. No vol, Journal or Pages cited.

Yang, Yili. Blood, vol. 89, No. 2, Jan. 15, 1997; pp. 550–557.

Estaquier, Jerome. Blood, vol. 87, No. 12, Jun. 15, 1996; pp. 4959–4966.

Kovacs, Joseph A., M.D. New England Journal of Medicine, vol. 332, No. 9, 1995; pp. 567–575.

*Primary Examiner*—Elizabeth Kemmerer
*Assistant Examiner*—Nirmal S. Basi

[57] ABSTRACT

An agent for preventing or treating AIDS which contains as its effective component an anti-Fas ligand antibody, and the method for preventing and treating AIDS by using such drug.

4 Claims, No Drawings

AGENT FOR SUPPRESSING A REDUCTION OF CD4+ LYMPHOCYTES

This invention is a continuation in part application of U.S. application Ser. No. 09/001,011, filed on Dec. 30, 1997, abandoned Apr. 17, 1999, which is a continuation of PCT/JP96/01820. PCT/JP96/01820 has been filed with the designated state of United States on Jul. 1, 1996 as a continuation in part application of Ser. No. 08/649,100, filed on May 17, 1996.

BACKGROUND OF THE INVENTION

This invention relates to a drug for preventing and treating AIDS which contains as its effective component a Fas antagonist which suppresses apoptosis induced by Fas—Fas ligand system, and in particular, an anti-Fas ligand antibody.

Fas is a cell surface antigen which transmits apoptosis signal to the cell, and Fas is recognized by Fas antibody (Yonehara, S. et al., J. Exp. Med. vol. 169, 1747–1756, 1989) which is a monoclonal antibody produced by immunizing a mouse with human fibroblast.

Human Fas ligand is a polypeptide which has been reported by Nagata et al. to be a biological molecule which induces apoptosis of Fas-expressing cells (Takahashi, T. et al., International Immunology, vol. 6, 1567–1574, 1994). Human Fas ligand is a Type II membrane protein of TNF family with a molecular weight of about 40 kD. As in the case of TNF, human Fas ligand in the human body is estimated to be in the form of a trimer (Tanaka, M. et al., EMBO Journal, vol. 14, 1129–1135, 1995). The extracellular domain of the human Fas ligand is highly homologous with the extracellular domain of rat Fas ligand (Suda, T. et al., Cell, vol. 75, 1169–1178, 1993) and mouse Fas ligand (Takahashi, T. et al., Cell, vol. 76, 969–976, 1994). The human Fas ligand recognizes not only the human Fas but also the mouse Fas to induce the apoptosis, and vice versa, the rat Fas ligand and the mouse Fas ligand also recognize the human Fas to induce the apoptosis.

Considerable researches have also been done on the mechanism of signal transduction in the cell upon the Fas-mediated apoptosis, and identification and cloning of the factor which interacts with the intracellular domain of the Fas, in particular, the region called "death domain" to transmit or block the signal have been reported. Possibility of the involvement of ICE (interleukin-1-converting enzyme)-related thiol proteases in the Fas-mediated apoptosis has also been indicated.

Acquired immune deficiency syndrome (AIDS) is a condition wherein human immunodeficiency virus (HIV) has targeted and infected CD4+ T lymphocytes and the destruction of the CD4+ T lymphocytes has induced serious immunodeficiency. AIDS is the terminal condition of the HIV infection subsequent to the asymptomatic stage and the following stage of various immunodeficiency symptoms. The term, HIV infection is a generic term including all of such stages.

Destruction of the CD4+ T lymphocytes inviting the onset of the AIDS has been formerly estimated to be the immediate result of the cell destruction by the HIV infection and virus propagation. Recent studies, however, have indicated the relation of the apoptosis with the decline in number of the CD4+ T lymphocytes. Kobayashi, N. (Jikken Igaku (Experimental Medicine), vol. 13, No. 16, 1981–1988, 1995) has reported that lymphocytes of the peripheral blood collected from patients suffering from HIV infection exhibit a Fas expression rate higher than that of the normal donor, and that the apoptosis is induced by the Fas stimulation in such lymphocytes in a period shorter than the normal donor. Okamoto, M. et al. (Igaku Kensa (Medical Tests), vol. 45, No. 12, 1693–1698, 1996) has proposed a possible mechanism for the decline in the number of T cells in the HIV infection that, in the case of the HIV infection, uninfected CD4+ T cells are activated to express the Fas, and the thus expressed Fas interacts with the Fas ligand from the HIV-infected monocytes or macrophages to induce the apoptosis. Nakanishi, Y. (Jikken Igaku (Experimental Medicine), vol. 15, No. 19 (Special Issue), 2449–2453, 1997), however, has reported that T lymphocytes of the peripheral blood collected from those suffering from HIV infection undergoes apoptosis even if macrophages were absent.

Estaquier, J. et al. (Blood, vol. 87, No. 12, 4959–4966, 1996) has demonstrated that the apoptosis induced by interacting the soluble Fas ligand with the CD4+ T cells or CD8+ T cells separated from the lymphocytes of the peripheral blood collected from those suffering from HIV infection could be suppressed by antagonistic anti-Fas antibody or Fas-Fc fusion protein. Yang, Y. et al. (Blood, vol. 89, No. 2, 550–557, 1997) has reported that in vitro spontaneous cell death of the lymphocytes of the peripheral blood collected from those suffering from HIV infection could be suppressed by Fas-Fc fusion protein.

HIV infection has been treated by using various reverse transcriptase inhibitors and/or protease inhibitors which are capable of inhibiting virus propagation. Such treatments often invited adverse actions such as vomiting, vomiturition, softening of feces, diarrhea, hepatopathy, pancreas damage, myelosupression, and among others, anemia and decline in the number of white blood cells, and such adverse actions were often quite serious. In addition, occasional appearance of the virus exhibiting resistance to such agents in the course of the treatment has made the treatment of the HIV infection quite difficult.

No suggestion has so far been made for the action of the transcriptase inhibitor or the protease inhibitor to suppress the apoptosis induced by the Fas—Fas ligand system which is responsible for the decline of T lymphocyte count in the HIV infected patient.

Use of an HIV neutralizing antibody for the treatment of the HIV infection has been proposed in Published Japanese Translation Nos. 3-504556 (WO 88/09181), 9-505466 (WO 95/11317), JP-A 6-217791 (WO 93/19785), and the like. The virus neutralizing antibody is expected to bind to the virus released from the infected cell to neutralize the infectivity of the virus, and effectivity of the virus neutralizing antibody in preventing the infection by HIV has been demonstrated in the infection experiment using chimpanzees as described in JP-A 6-217791 (WO 93/19785). The HIV neutralizing antibody, however, would not be suitable for use in the removal of the infected T cells, and virus surface antigens are also known to undergo mutations which results in reduced binding with the antibody. In addition, there has so far been no indication for the HIV neutralizing antibody to suppress the apoptosis induced by the Fas—Fas ligand system which is one of the mechanisms for the decline of T lymphocyte count in the HIV infected patient.

JP-A 2-237935 discloses that growth of the HIV-infected cell line had been suppressed in an in vitro experiment by the anti-Fas antibody (agonistic anti-Fas antibody) which induces apoptosis by binding to Fas on the cell surface. JP-A 2-37935 also proposes a drug for treating AIDS containing such agonistic anti-Fas antibody. WO 97/12632 discloses use of the Fas ligand or the agonistic anti-Fas antibody for promoting the apoptosis in the treatment of virus infections caused by HIV or herpes simplex virus (HSV)-2. Such induction of apoptosis of the HIV-infected cells by using the agonistic anti-Fas antibody is associated with the risk of simultaneous induction of apoptosis of the HIV-uninfected Fas$^+$CD4$^+$ T cells, inviting further decline of the CD4$^+$ T cell count in the HIV-infected patients to worsen the disease conditions.

WO 95/13293 (EP 675200) and WO 96/29350 proposes treatment of AIDS, hepatitis and rheumatism by using the anti-Fas ligand antibody. WO 97/02290 (PCT/JP96/01820) which is the parent application of the present application proposes use of the anti-Fas ligand antibody for the inhibition of the apoptosis by the Fas—Fas ligand system in the diseases which are expected to be associated with excessive apoptosis such as autoimmune diseases (rheumatism, SLE, and diabetes), virus infections (influenza and AIDS), hepatitis, rejection in organ transplantation, graft versus host disease, ulcerative colitis, Crohn's disease, and the like.

It is, however, not yet clear whether the Fas—Fas ligand system in the case of HIV infection is involved in the mechanism of removal of the HIV-infected cells or in the mechanism of death of the T cells. In the former case, hyperfunctioning of the Fas—Fas ligand system would be desirable in contrast to the latter case wherein the inhibition of the Fas—Fas ligand system is desirable. There is no specific report with regard to the effectivity of the anti-Fas ligand antibody for the HIV infection. In addition, Okumura, K. et al. (1997 Project for Promoting the AIDS Pharmaceuticals Development, International Research Grant Project, Research Report, 113–122, 1997) has reported that the anti-Fas ligand antibody failed to block anti-CD3 antibody-induced apoptosis of CD4$^+$ T cells or CD8$^+$ T cells from HIV-infected individuals, and indicated the presence of a mechanism other than the one involving the Fas—Fas ligand system for the apoptosis of T cells in the patients suffering from the HIV infection.

Published Japanese Translation Nos. 8-511692 (WO 95/27735) and 9-503672 (WO 95/10540) describe an inactivated Fas ligand analogue and antagonistic anti-Fas antibody as apoptosis inhibitory substances involving the Fas—Fas ligand system other than the anti-Fas ligand antibody. These publications, however, also fail to specifically refer to the HIV infection.

Effectivity of a prophylactic or therapeutic agent for AIDS can not be evaluated solely by in vitro experiments. For example, interleukin-2 is known to have an in vitro ability to proliferate the lymphocytes of peripheral blood collected from the patient infected with HIV. Kovacs, J. A. et al. (N. Engl. J. Med., vol. 332, No. 9, 567–575, 1995) administered the interleukin-2 to the patents infected with HIV. Increase in the CD4$^+$ T cells was observed in some of the patients while further virus activation as well as drug adverse actions were observed in most of the patients with no immunological improvement. The results expected from the in vitro results were not at all reproduced in the in vivo experiment.

An object of the present invention is to provide a drug for preventing and treating HIV infection which prevents the decline of lymphocyte count by inhibiting the Fas antigen-mediated apoptosis. Another object of the present invention is to provide a method for preventing and treating HIV infection by utilizing such a drug. More specifically, the object of the present invention is to provide a drug for preventing and treating AIDS which contains as its effective component anti-Fas ligand antibody.

SUMMARY OF THE INVENTION

The inventors of the present invention have been engaged in intensive study on the role of the Fas antigen and the Fas antigen-mediated apoptosis in HIV infections, and found that the decline of lymphocyte count in HIV infection is suppressed by an apoptosis-inhibitory Fas antagonist, and in particular, by the anti-Fas ligand antibody. The present invention has been completed on such a finding.

The present invention provides an agent for preventing and/or treating AIDS which contains a Fas antagonist as its effective component. In the agent or drug of the present invention, the Fas antagonist inhibits apoptosis of the lymphocytes in the HIV infection. The Fas antagonist is a member selected from a Fas derivative, anti-Fas antibody, and anti-Fas ligand antibody. Preferably, the Fas antagonist is anti-Fas ligand antibody, and in particular, the anti-Fas ligand antibody is a humanized anti-Fas ligand antibody. The drug for preventing and treating AIDS of the present invention is preferably used for preventing and treating the conditions of the lymphocyte count decline in the advancement of the HIV infection. This invention provides a drug for preventing and/or treating HIV infection, and in particular, a novel use of the anti-Fas ligand antibody as a drug for preventing and/or treating AIDS as well as the method for preventing and/or treating such diseases.

The present invention also provides a drug for preventing and treating a disease associated with the decline of T cell count, and in particular, CD4$^+$ T cell count, as well as a novel use of the anti-Fas ligand antibody as a drug for preventing and treating a disease wherein the decline of the CD4$^+$ T cell count leads to an immunodeficiency.

It should be noted that the term "Fas antagonist" used herein designates a substance having a suppressive or inhibitory action, and in particular, a substance which suppresses or inhibits the biological action of the Fas/Fas ligand system, and in particular, the Fas antigen-mediated apoptosis of the cells.

DETAILED DESCRIPTION OF THE INVENTION

The Fas antagonist described herein is not limited to any particular type as long as it somehow blocks the signal generation or transduction by the Fas antigen and inhibits the biological action of the Fas/Fas ligand system, and in particular, the Fas antigen-mediated apoptosis, and more particularly, the Fas antigen-mediated apoptosis wherein Fas ligand is involved. Fas antagonists of various action mechanisms may be used in the present invention, and the exemplary Fas antagonists include those inhibiting the action or function of the Fas ligand or the Fas antigen; those interacting with the extracellular domain of the Fas ligand or the extracellular domain of the Fas antigen; those inhibiting the interaction of the Fas ligand and the Fas antigen; those affecting the interaction between the intracellular domain of the Fas antigen and intracellular element interacting with the Fas antigen intracellular domain; and those inhibiting the action of the intracytoplasmic factor such as ICE (interleukin-1 converting enzyme) like protease which is involved in the signal transduction in the Fas antigen-mediated apoptosis. The antagonist may be either a high molecular weight proteinaceous substance or a low molecular weight compound. More specifically, the term antagonist used herein encompasses any antagonist which has the action of inhibiting the Fas antigen-mediated apoptosis, and includes a Fas antigen derivative, anti-Fas ligand antibody, antagonistic anti-Fas antibody, an antisense oligonucleotide for the gene or mRNA of Fas antigen or Fas ligand, a substance which interacts with the intracellular domain of Fas antigen, an ICE inhibitor, and the like. In this context, the Fas antigen and the Fas ligand are preferably those derived from human. The Fas antagonist described herein is preferably the one which suppresses the apoptosis of the Fas antigen-expressing cell in an adequate assay described in International Patent Application Publication No. WO 95/13293 (EP 675200).

It should be noted that the U.S. patent application Ser. No. 08/649100 and the International Patent Application Publication Nos. WO 95/13293, WO 97/02290, WO 90/07861, and WO 92/11018 are incorporated herein by reference.

The antibody used in the present invention may be either a polyclonal antibody or a monoclonal antibody, and the molecular species used in the present invention is not particularly limited. The antibody used in the present invention may be either an antibody molecule of normal form or a fragment thereof which is capable of binding to the antigen to inhibit the Fas antigen-mediated apoptosis, for example, Fab, F(ab')$_2$, Fv, or single chain Fv (scFv) which is the Fv of heavy chain linked to the Fv of light chain by an adequate linker to form a single chain. In addition, the antibody used in the present invention may be an immunoglobulin of any class, subclass or isotype. As described above, the antibody used in the present invention is not limited any particular type as long as is capable of binding to the Fas ligand or the Fas antigen to inhibit the biological actions of the Fas/Fas ligand system, and in particular, the Fas antigen-mediated apoptosis.

The Fas antagonist may preferably be a Fas antigen derivative, antagonistic anti-Fas antibody or anti-Fas ligand antibody, and in the present invention, use of the anti-Fas ligand antibody is most preferable.

The anti-Fas ligand antibody used in the present invention may be an antibody of any type (either monoclonal or polyclonal) and any origin produced by any appropriate process. The anti-Fas ligand antibody, however, is preferably a monoclonal antibody derived from a mammal. The monoclonal antibody used in the present invention may be produced in any animal species so long as it is a mammal which may be human or non-human. The monoclonal antibody from a mammal other than human may be the one from rabbit or other rodents. The non-limiting preferable examples of such rodents are mouse, rat and hamster, and use of such animals facilitates a convenient production of the monoclonal antibody. Furthermore, the monoclonal antibody may be the one which is capable of recognizing the antigen in a conventional immunoprocess such as radioimmunoassay (RIA), enzyme immunoassay (EIA, ELISA), immunofluorescent analysis, or the like, and whose activity of suppressing the apoptosis of the Fas antigen-expressing cell is measurable by an appropriate assay described in International Patent Application Publication No. WO 95/13293 (EP 675200), WO 97/02290, or the like.

The anti-Fas ligand antibody is, for example, an antibody which exhibits an apoptosis suppression as measured by the assay using the release of $^{51}$Cr for the index ($^{51}$Cr release assay) as described in Examples 1–3 of WO 97/02290 of preferably 50% or higher, and more preferably 90% or higher.

$$\text{Apoptosis suppression rate (\%)} = \frac{\text{Radioactivity of the control group} - \text{Radioactivity of the antibody-treated group}}{\text{Radioactivity of the control group}} \times 100$$

More illustratively, the anti-Fas ligand antibody is an antibody which exhibits an apoptosis suppression rate of 50% or higher at 1 µg/ml, and in particular, at 0.3 µg/ml.

Among these, an example of the most preferable anti-Fas ligand antibody is mouse F919-9-18 antibody produced by hybridoma F919-9-18 which was originally deposited on Jun. 22, 1995 in National Institute of Bioscience and Human Technology, Agency of Industrial Science and Technology (1-3, Higashi 1-chome, Tsukuba-shi, Ibaraki-ken, Japan) (Accession No. P-15002) and transferred from the original deposition to the international deposition on May 9, 1996 (Accession No. FERM BP-5535).

Another example of the preferable anti-Fas ligand antibody is the antibody which inhibits the binding of the Fas ligand and the mouse F919-9-18 antibody, and in particular, the antibody which recognizes the epitope which is the same as the epitope recognized by the mouse F919-9-18 antibody.

In addition, the anti-Fas ligand antibody used in the present invention is preferably a chimeric antibody which is an antibody intentionally altered for the purpose of reducing heteroantigenicity to human. An exemplary such chimeric antibody is a chimeric antibody comprising the variable region from the monoclonal antibody of a mammal other than human such as mouse, and the constant region from the human antibody. Such chimeric antibody may be produced by a known chimeric antibody production process, and in particular, by a genetic engineering process.

More preferably, the anti-Fas ligand antibody used in the present invention is a reshaped human antibody wherein complementarity determining region (CDR) of the human antibody is replaced with the complementarity determining region derived from the antibody of a mammal other than human such as mouse. A preferable example of the reshaped human antibody (humanized antibody) is humanized F919 antibody having the CDR derived from the murine F919-9-18 antibody, which is disclosed in WO 97/02290. Specific examples are HuF919G1.v1, HuF919G1.v2, HuF919G4.v1, and HuF919G4.v2 described in WO 97/02290.

It should be noted that, if necessary, an amino acid in the framework (FR) sequence in the variable region of the antibody may be substituted with another amino acid so that the complementarity determining region of the humanized antibody would form an adequate antigen-binding site.

The anti-Fas ligand antibody used in the present invention may be prepared, for example, by the process described in WO 95/13293 (EP 675200) and WO 97/02290.

When a monoclonal antibody is used in the present invention, such monoclonal antibody may be prepared by the process known in the art, for example, by using Fas antigen, Fas ligand, or a partial peptide thereof for the immunization antigen, immunizing an animal with such antigen in accordance with a conventional process, fusing the resulting immunized cell with a known parent cell by a conventional cell fusion process, and screening for the monoclonal antibody-producing cell by a conventional screening process.

More illustratively, when the immunization antigen is human Fas ligand, the nucleotide sequence of the human Fas ligand disclosed in Takahashi, T. (International Immunology, vol. 6, pages 1567 to 1574, 1994) is used, and this nucleotide sequence is inserted in a known expression vector system to transform an adequate host cell, the desired Fas ligand protein is obtained by the purification from the transformed cell themselves or the supernatant of the transformed cell culture, and the thus obtained purified Fas ligand protein is used for the immunization antigen.

The mammal which may be immunized with the immunization antigen is not limited to any particular type, and may be selected by considering the compatibility with the parent cell used in the cell fusion. The exemplary animals are mouse, rat, hamster, and rabbit.

The immunization of the animal with the immunization antigen may be carried out by a known procedure. After the immunization and confirmation of the increase of the serum level of the desired antibody, the immunocytes are isolated from the animal, and subjected to cell fusion. The preferable immunocytes are splenocytes.

The parent cell to be fused with the immunocyte is not limited to any particular type. However, use of a known mammal myeloma cell line, and in particular, a mouse myeloma cell line such as X63.653 (P3x63Ag8.653) (J. Immunol. 123: 1548, 1978) is preferred. The cell fusion of the above-described immunocyte and the myeloma cell may be carried out basically in accordance with a known procedure such as the process of Milstein et al. (Milstein et al., Methods Enzymol. 73: 3–46, 1981).

The screening of the hybridoma which produces the desired antibody may be carried out by a known procedure, then the cloning of the (selected) hybridoma may be carried out by a known procedure.

The monoclonal antibody is obtained from the thus prepared hybridoma producing the monoclonal antibody used in the present invention by cultivating the hybridoma according to the conventional method and obtaining the monoclonal antibody from the supernatant; or by transplanting the hybridoma to a mammal compatible with the hybridoma for propagation, and obtaining the monoclonal antibody from the ascite of the mammal. The former procedure is adapted for producing the monoclonal antibody of high purity, and the latter process is adapted for producing the monoclonal antibody in a large amount.

The monoclonal antibody produced by such procedure for use in the present invention may be further purified by a known purification means such as salt precipitation, gel filtration, affinity chromatography, and the like.

The monoclonal antibody used in the present invention is not limited to the one produced by using a hybridoma, and may be the one produced by an antibody-producing cell immotalized by EBV and the like or the one produced by a genetic engineering procedure.

The humanized antibody used in the present invention may be prepared in accordance with Reichmann, L. et al. (Nature 332: 323 (1988)), and EP-A-0239400; Queen, C. et al. (Proc. Natl. Acad. Sci. USA 86: 10029 (1989)), WO 90/07861 and WO 92/11018; Co, M. S. et al. (Proc. Natl. Acad. Sci. USA, 88: 2869 (1991)); Co, M. S. and Queen, C. (Nature 351: 501 (1991)); and Co, M. S. et al. (J. Immunol. 148: 1149 (1992)), which are herein cited by reference.

The characteristic feature of the AIDS-preventing and treating drug of the present invention is its inclusion of a Fas antagonist, and most preferably, an anti-Fas antibody. The AIDS-preventing and treating drug of the present invention may be in the form of a pharmaceutical composition or kit such as an injection or an oral medicine wherein the Fas antagonist is combined with at least one pharmaceutical carrier or medium such as sterilized water, physiological saline, a vegetable oil, a mineral oil, a higher alcohol, a higher fatty acid, or a nontoxic organic solvent; and optional additives such as a diluent, coloring agents, an emulsifier, a suspending agent, a surfactant, a solubilizer, an adsorption-preventing agent, a stabilizer, a preservative, a moisture retention agent, an antioxidative, a buffering agent, an isotonizing agent, and a soothing agent. Preferably, the AIDS-preventing and treating drug of the present invention is parenterally administered either systemically or locally, and rapidly or gradually, for example, by intravenous, intramuscular, intraperitoneally, or subcutaneous injection. The AIDS-preventing and treating drug of the present invention should be administered at an adequate dose determined by taking the conditions and age of the patient as well as the administration route into consideration. For example, an adequate divided dose may be selected in the range of approximately 1 to 1000 mg/individual. The AIDS-preventing and treating drug of the present invention, however, is not limited to the administration route and the dose as described above. The AIDS-preventing and treating drug of the present invention may also contain a combination or two or more Fas antagonist, and may be used in combination with another drug. Furthermore, the AIDS-preventing and treating drug of the present invention may be used in combination with another therapeutic agent for HIV infection which acts in a mechanism different from that of the present invention.

The AIDS-preventing and treating drug of the present invention may be formulated into a pharmaceutical preparation in a normal process. For example, an injection may be prepared by dissolving the purified anti-Fas ligand antibody in a medium such as physiological saline or a buffer and optionally supplementing the solution with an additive such as an anti-adsorptive. The preparation may also be in the form of a lyophilizate which is to be reconstituted before the use, and may contain any of the excipients that are generally used for facilitating the lyophilization.

An in vivo experiment was conducted by using rhesus monkey AIDS model to confirm the efficacy of the AIDS-preventing and treating drug of the present invention containing the anti-Fas ligand antibody as its effective component. Simian immunodeficiency virus (SIV) is a virus similar to HIV which is known to be found in simians. Reimann, K. A. et al. (J. Virol., Vol. 70, No. 10, 6922–6928 (1996)) have reported that inoculation of SHIV which is an HIV-SIV chimeric virus invites decline in CD4$^+$ T cell count as well as wasting and opportunistic infections like those of the AIDS. When the AIDS-preventing and treating drug of the present invention containing the anti-Fas ligand antibody as its effective component was administered to the rhesus monkey inoculated with SHIV, the decline in CD4$^+$ T cell count was inhibited to confirm the in vivo efficacy of the drug.

The AIDS-preventing and treating drug of the present invention, when administered to a patient suffering from HIV infection, inhibits decline of lymphocytes, and in particular, decline of lymphocytes which increases expression of Fas to thereby prevent progression of the immunofunction failure associated with the HIV infection.

The AIDS-preventing and treating drug of the present invention is also effective in alleviating fever, pharyngeal pain, swelling of lymph nodes, diarrhea, weight loss, malaise, night sweat, cranial neuropathy, and the like, and preventing and treating opportunistic infections, malignant tumors such as Kaposi sarcoma, and demantia of AIDS-related type associated with the progression of the HIV infection.

The AIDS-preventing and treating drug of the present invention may be administered to an asymptomatic carrier (AC) who is positive for anti-HIV antibody but who exhibits only slight decline in CD4 cell count and who is almost as healthy as normal people; in the case of AIDS-related complex (ARC) exhibiting continuous decline in CD4 cell count and immunofunction failure showing various immunodeficiency conditions; and in the case of AIDS with serious immunodeficiency conditions associated with opportunistic diseases and malignant tumors such as Kaposi sarcoma.

The AIDS-preventing and treating drug of the present invention may also be administered for prophylactic purpose to those who are HIV negative but who are likely to be exposed to HIV, and to those who are seronegative after recovering from the HIV positive state to thereby prevent relapsing.

Next, the present invention is described in further detail by referring to Examples which by no means limit the scope of the present invention.

EXAMPLES

Example 1
Toxicity test of anti-Fas ligand antibody
(1) Method

Male DBA/1J and C3H/He mice of 8 week old (Charles River Japan) were used. The anti-mouse Fas ligand antibody described in PCT/JP97/03978 which is herein incorporated by reference was administered from the tail vein of the mouse at 100 mg/30 ml/kg. The mice belonging to control group were administered with physiological saline (Otsuka Pharmaceutical Co., Ltd.) from the tail vein at 30 ml/kg. For both strains, n was 3 for each group. The mice were observed for 7 days and body weight measurement, hematology test (red blood cell, white blood cell, and platelet), blood biochemistry test (GOT, GPT and urea nitrogen), and autopsy with naked eye were conducted.

(2) Results

No significant difference were observed between the groups treated with the anti-mouse Fas ligand antibody and the control groups in the body weight increase after administration, the hematological measurements (red blood cell, white blood cell, and platelet), and the blood biological measurements (GOT, GPT and urea nitrogen). In addition, no abnormality was observed in the autopsy with naked eye for the groups treated with the anti-mouse Fas ligand antibody.

Example 2
Effect of humanized anti-human Fas ligand antibody in suppressing the decline in number of $CD4^+$ T cells in rhesus monkey AIDS model
(1) Preparation of AIDS model Ten male rhesus monkeys (body weight: 2.4 kg to 2.9 kg) (purchased from Oregon Regional Primate Research Center) were employed for the experiment. Absence of abnormality was confirmed in 6 week quarantine by a routine method. Stock solution of SHIV-89.6 (purchased from Virus Research Institute in the U.S.; J. Virology, vol. 70, pages 6922–6928, 1996) which is a chimera virus of simian immunodeficiency virus (SIV) and human immunodeficiency virus (HIV) was diluted 1000 times, and 1 mL of the above diluted solution of SHIV-89.6 was intravenously administered.

(2) Administration of AIDS-preventing and treating drug containing anti-Fas ligand antibody as its effective component.

Humanized F919 antibody was used as a solution in citric acid buffer (20 mM citric acid, 120 mM sodium chloride, 0.01% Tween 80, pH 6.0). The rhesus monkeys were divided into two groups by using the body weight as a parameter, the control group and the humanized F919 antibody treatment group each comprising 5 individuals. The humanized F919 antibody was intravenously administered at a dose of 10 mg/kg simultaneously with the inoculation of the SHIV-89.6p (day 1). The control group was intravenously administered with the same volume of the citric acid buffer. The administration was conducted once a week.

(3) Blood collection and analysis by FACS

The animals were anaesthetized by intramuscularly injecting 10 mg/kg of ketamine hydrochloride, and the blood was collected from the vein in the presence of EDTA. The blood collection was conducted immediately before the inoculation of SHIV-89.6, and immediately before the administration of the drug at day 8 and day 15. To the thus collected 100 μL of blood supplemented with EDTA was added 10 μL of OKT4a antibody (Ortho) which specifically recognizes $CD4^+$ T cells, and the blood was allowed to stand in a dark place for 10 minutes, and the blood was further supplemented with 2 mL of FACS solution (Becton Dickinson) and allowed to stand at room temperature for another 10 minutes. The blood was then washed with minimum essential medium containing 5% of bovine fetal serum, and fixed with 0.5% formaldehyde. The specimen was analyzed by FACScanT (Becton Dickinson) and percentage of the $CD4^+$ T cells was calculated in relation to total lymphocytes count in peripheral blood.

(4) Results

Average values of the percentage of $CD4^+$ T cells before the inoculation of the SHIV-89.6 in the control group and the humanized F919 antibody treatment group were 29.7% and 28.7%, respectively. In the control group, the value somewhat declined to 26.5% at day 8, and drastically declined to 6.9% at day 15. In contrast, in the humanized F919 antibody treatment group, the value was 29.2% at day 8 and 14.1% at day 15, demonstrating the effect of the humanized F919 antibody in suppressing the decline of $CD4^+$ T cell percentage. It should be noted that no significant toxicity induced by the humanized F919 antibody treatment was observed.

|  | Percentage of $CD4^+$ T cells | | |
| --- | --- | --- | --- |
|  | Before inoculation | Day 8 | Day 15 |
| Treatment group | 28.7% | 29.2% | 14.1% |
| Control group | 29.7% | 26.5% | 6.9% |

As evident from the results as described above, the drug for preventing and treating AIDS of the present invention exhibits excellent efficacy without exhibiting any significant toxicity. The drug for preventing and treating AIDS containing the anti-Fas ligand antibody of the present invention is effective in treating the HIV infection as long as the Fas—Fas ligand system is involved in the infection since the drug blocks signal generation or transduction by the Fas antigen to inhibit biological actions of the Fas—Fas ligand system, and in particular, the death of lymphocytes by the Fas antigen-mediated apoptosis.

The drug for preventing and treating AIDS of the present invention containing the anti-Fas ligand antibody as its effective component inhibits biological actions of the Fas—Fas ligand system, and in particular, the death of lymphocytes by the Fas antigen-mediated apoptosis. Accordingly, the AIDS-preventing and treating drug of the present invention containing the anti-Fas ligand antibody as its effective component is expected to serve a prophylactic and therapeutic drug for the HIV infections associated with the decline of lymphocyte counts by apoptosis.

What is claimed is:

1. A pharmaceutical composition for suppressing a reduction of CD4$^+$ lymphocytes comprising the anti-Fas ligand antibody humanized F919 antibody.

2. A method for suppressing a reduction in CD4$_+$ lymphocytes which comprises:

administering an effective amount of a purified anti-Fas ligand antibody comprising a CDR (complementarity determining region and an FR (frame work region), which binds to Fas ligand through at least a CDR and which is an antagonist of Fas ligand.

3. The method for suppressing a reduction in CD4$_+$ lymphocytes according to claim 2 wherein said anti-Fas ligand antibody is a humanized anti-Fas ligand antibody in which a portion of said FR (frame work region) is derived from human.

4. The method for suppressing a reduction in CD4$_+$ lymphocytes according to claim 3 wherein said anti-Fas ligand antibody is humanized F919 antibody.

* * * * *